(12) United States Patent
Workman et al.

(10) Patent No.: US 8,361,322 B2
(45) Date of Patent: Jan. 29, 2013

(54) IMPREGNATED EXPANDED POLYTETRAFLUOROETHYLENE (EPTFE) TUBING AS A STATIONARY PHASE

(75) Inventors: Stephen M. Workman, Fort Collins, CO (US); Robert T. Shannon, Denver, CO (US)

(73) Assignee: ALS Group USA, Corp, Houston, TX (US)

( * ) Notice: Subject to any disclaimer, the term of this patent is extended or adjusted under 35 U.S.C. 154(b) by 52 days.

(21) Appl. No.: 13/082,149

(22) Filed: Apr. 7, 2011

(65) Prior Publication Data
US 2011/0186520 A1 Aug. 4, 2011

Related U.S. Application Data

(62) Division of application No. 12/202,850, filed on Sep. 2, 2008.

(51) Int. Cl.
*B01D 15/32* (2006.01)

(52) U.S. Cl. ........ 210/669; 210/662; 210/650; 210/651; 210/649

(58) Field of Classification Search .................. 210/649, 210/650, 651, 669, 662
See application file for complete search history.

(56) References Cited

U.S. PATENT DOCUMENTS

| | | | |
|---|---|---|---|
| 4,256,631 A | 3/1981 | Yokoo et al. | |
| 5,441,643 A | 8/1995 | Spears et al. | |
| 6,214,232 B1 | 4/2001 | Baurmeister et al. | |
| 6,277,489 B1 | 8/2001 | Abbott et al. | |
| 6,511,603 B1 | 1/2003 | Dietz et al. | |
| 6,603,127 B1 | 8/2003 | Scheinberg et al. | |
| 7,157,022 B2 | 1/2007 | Horwitz et al. | |
| 2003/0068317 A1* | 4/2003 | Lee et al. | 424/140.1 |
| 2005/0023221 A1 | 2/2005 | Marcus | |
| 2006/0011543 A1 | 1/2006 | van Strien et al. | |
| 2006/0201881 A1 | 9/2006 | Marcus et al. | |
| 2007/0131618 A1 | 6/2007 | Horwitz et al. | |

OTHER PUBLICATIONS

Murakami, Masahiko and Furata, Naoki, "Novel Preconcentration Technique Using bis(2-ethylhexyl) Hydrogen Phosphate (HDEHP) Loaded Porous Polytetrafluoroethylene (PTFE) Filter Tube as a Sorbent: Its Application to Determination of In(III) in Seawater by ICP-MS with Air Segmented Discrete Sample Introduction," Analytica Chimica Acta 556 (2006) pp. 423-429.

Murakami, Masahiko and Takada, Takeo, "Novel Sorbent Extraction Technique Using a Chelating Agent Impregnated Porous PTFE Filter Tube: Preconcentration of IN (III) with a bis(2-ehtylhexyl) Hydrogen Phosphate (HDEHP) Loaded Porous PTFE Filter Tube," Department of Chemistry, Apr. 1999, pp. 185-188.

Horwitz, E. Philip, et al., "A Novel Strontium-Selective Extraction Chromatographic Resin," Chemistry Division, Argonne National Laboratory, vol. 10, No. 2, 1992, pp. 1-29.

* cited by examiner

*Primary Examiner* — Nam Nguyen
*Assistant Examiner* — Denise R Anderson
(74) *Attorney, Agent, or Firm* — Craig Metcalf; Kirton McConkie (57) ABSTRACT

A solid-phase extraction device utilizing a section of expanded polytetrafluoroethylene (ePTFE) tubing as the stationary phase is disclosed. The microscopic pores of ePTFE tubing are impregnated with a binding agent having an affinity for a target constituent within a matrix. The matrix is prepared and loaded onto the stationary phase of the system. The target constituent is retained by the stationary phase. The constituent is stripped from the stationary phase with a stripping solution, and collected for further analysis or use.

18 Claims, 5 Drawing Sheets

IMPREGNATED EXPANDED POLYTETRAFLUOROETHYLENE (EPTFE) TUBING AS A STATIONARY PHASE

RELATED APPLICATIONS

This application is a divisional patent application of U.S. patent application Ser. No. 12/202,850, filed Sep. 2, 2008, entitled IMPREGNATED EXPANDED POLYTETRAFLUOROETHYLENE (ePTFE) TUBING AS A STATIONARY PHASE, and which is incorporated herein.

BACKGROUND OF THE INVENTION

The present disclosure relates to solid-phase extraction. Specifically, the present disclosure relates to the use of expanded polytetrafluoroethylene (ePTFE) tubing as a stationary phase of a solid-phase extraction system.

The ability to extract a targeted analyte from a material has proven to be of great assistance in a variety of applications. For instance, the ability to assay the contents of test samples by targeted extraction of a specific constituent or constituents from a sample material has proven extremely useful in the testing and examination of biological and environmental samples. Similarly, chemical separation schemes often require the separation of one or more target constituents from a fluid to yield a desired purified product. For example, a short-lived radionuclide or radionuclides present together as decay progeny may be separated from the respective parent radionuclide(s) to permit use as an analytical standard, in a radiopharmaceutical, or as a component in a subsequent process. Often, when the constituent or constituents are not present in a physical or chemical state amenable to chemical separation, extensive physical or chemical preparation may be required prior to the chemical separation or final use. The preparation steps may include different combinations of physical processes, such as physical size reduction or filtering of particulates from a fluid, and chemical processes such as combustion or ignition, dissolution of a solid, or reaction with various chemical reagents to obtain a fluid containing the target constituents in physical and chemical forms that are amenable to the separation to be performed.

The ability to purify one constituent of a material by selectively removing unwanted components from a fluid also has an abundance of useful applications in the testing and examination of biological and environmental samples and in other more general settings. For example, radioanalytical separation schemes may require removal of interfering constituents in a solution to yield a desired purified product. Similarly, parent radionuclides may need to be separated from short-lived decay progeny to allow the use of progeny species as analytical standards, in radiopharmaceuticals, or as input materials for a second process. Often, when the constituent or constituents are not present in a physical or chemical state amenable to chemical separation, extensive physical or chemical preparation may be required prior to the chemical separation or final use. The preparation steps may include different combinations of physical processes, such as physical size reduction or filtering of particulates from a fluid, and chemical processes such as combustion or ignition, dissolution of a solid, or reaction with various chemical reagents to obtain a fluid containing the target constituents in physical and chemical forms that are amenable to the separation to be performed.

Traditional solid-phase extraction systems utilize a stationary phase of resins or fibers to separate a targeted set of analytes or constituents from a fluid sample. The resins or fibers of these systems contain a binding agent having an affinity for the targeted constituents. The resins or fibers are then packed into an outer sleeve, such as a column or micropipette tip.

Several problems exist with traditional extraction systems. For example, one important limitation of traditional solid-phase extraction systems is that the stationary phase must remain surrounded in liquid to prevent air gaps and fissures in the packed resins or fibers from disrupting the functionality of the extraction system. Additionally, the process of packing the resins or beads is often a time consuming, delicate procedure involving multiple steps. Furthermore, some traditional systems require long equilibration periods or high pressures to move a sample through the stationary phase. Finally, the complexities and encumbering processes of traditional solid-phase extraction systems are costly both in time and resources thereby confining the use of the systems to a well-equipped laboratory.

What is needed in the art is an improved stationary phase and solid-phase extraction system that is both useful in a laboratory setting as well as transportable and efficient in extracting or purifying one or more targeted constituents and that is amenable to use with a wide range of extractants. Additionally, a stationary phase is needed that does not require constant immersion in a liquid and that does not require lengthy equilibration periods or high pressures to operate.

BRIEF SUMMARY OF THE INVENTION

The systems and methods of the present disclosure have been developed in response to problems and needs in the art that have not yet been fully resolved by the currently available solid-phase extraction systems. Thus, these systems and methods are developed to provide for a more efficient solid-phase extraction system.

One aspect of the present disclosure provides a solid-phase extraction system comprising a stationary phase, a mobile phase, and a collection vial. The stationary phase comprises a section of expanded polytetrafluoroethylene (ePTFE) tubing impregnated with a binding agent. The ePTFE tubing comprises a plurality of microscopic pores. The binding agent is impregnated within the plurality of microscopic pores by exposing the ePTFE tubing to the binding agent, by itself, or dissolved in a suitable solvent or mixture of solvents. For example, hydrophobic liquids such as acetone, hexane, octanol, or combinations of these and other hydrophobic liquids may be used. Additionally, the hydrophobic solution may be forced through the microscopic pores of the ePTFE tubing via a pressure differential created with a pump, a syringe, gravity, or other suitable means. The binding agent is selected to optimize affinity to a target analyte or constituent in the load solution. For example, binding agents may include aliphatic quaternary amines (e.g., tricaprylyl-methylammonium chloride [Aliquat-336®], triisotylamine [TIOA], trinoctylamine, [TnOA]), organophosphate complexing agents (such as octyl(phenyl)-N,N-diiso-butylcarbamoyl-methylphosphine oxide [CMPO]; tributylphosphate (TBP), trioctylphosphinic oxide (TOPO)), chelating agents, crown ethers, antibodies, or other binding agents found suitable for the purposes of the separation to be conducted.

The matrix may include any number of matrices including urine, blood, water samples, soil, beverages, animal tissues, consumer products, and modified or unmodified aqueous solutions or leachates or digestates of other solid or liquid matrices that contain the target constituents. Conceptually, the matrix may contain the constituent(s) of interest including any element(s) on the periodic table, or isotope on the chart of the nuclides, in any form (e.g., element, ion, complex, chelate, or compound) that is chemically or physically active with regard to the selected binding agent. For example, the matrix may contain any actinide, lanthanide, transition metal, halide, alkaline earth or alkaline metal, noble gas, or any other element, or ions, complexes or chelates thereof, with an affinity for the selected binding agent. Isotopic constituents are also commonly encountered in the area of analytical chemistry, including various isotopes or radioisotopes of carbon, zinc, mercury, copper, cadmium, chlorine, beryllium, mercury, strontium, manganese, cobalt, nickel, copper, zinc, gadolinium, germanium, arsenic, selenium, bromine, palladium, tin, antimony, tungsten, thallium, gold, platinum, astatine, iodine, lead, iron, francium, radium, barium, yttrium, lanthanum, cerium, neodymium, promethium, samarium, europium, thorium, uranium, americium, plutonium, curium, polonium, bismuth, magnesium, calcium, rubidium, cesium, thallium, actinium, iodine, chlorine, phosphorus, and mixtures thereof. Additionally, the matrix may contain any combination or modification of the above described constituents elements. For example, constituents may be incorporated in natural or synthetic compounds comprising additional undisclosed elements. Finally, the constituents may include organic compounds and biological compounds as well as other molecular compounds useful in immunoassay and radioimmunoassay techniques.

Prior to loading onto the stationary phase, the matrix may require treatment to ensure that the target constituents are transformed to, and maintained in, a physical and chemical state that facilitates its association with the binding agent and which may minimize or eliminate the effects of interfering or competing constituents and reactions. While the constituents in certain matrices may be in appropriate form such as to permit loading without preparation, other matrices, for example, require treatment with one or more preparatory agents to create a solution containing the constituents in a form appropriate to the chemical separation desired and the binding agent selected to effect the separation. Common preparatory agents include acids, bases, oxidizing or reducing agents, as well as complexing or chelating agents such as EDTA or DTPA or other such reagents as are needed to facilitate the separation being performed. For example, where the solid-phase extraction is based on an anion exchange, the matrix may be treated with an acid to form anions that have an affinity for the binding agent. Conversely, where the solid-phase extraction is based on a chelation, the matrix may be treated with appropriate preparatory agents to facilitate the desired chelation. Once all preparation is complete, the resulting solution is called the 'load solution'.

The load solution may consist of modified or unmodified aqueous solutions, leachates, or digestates of other matrices, such as solids or liquids, which contain the constituents of interest. The load solution may be loaded onto the stationary phase via any other means that creates a pressure differential between the inner and outer walls of the ePTFE tubing sufficient to cause of the load solution to flow through the impregnated pores of the tubing. Methods that may be used include a syringe, a pump, a vacuum source, or even gravity. Once in the system, the load solution comprises the mobile phase of the solid-phase extraction system. As the load solution is forced through the microscopic pores of the ePTFE tubing, the processed load solution, less any constituents removed on the stationary phase, and after passing through the walls of the tubing, collects on the external surface of the tube as droplets that may be recirculated through the same system or collected as product or as waste. The solution, once processed, may be further processed by a secondary device or analyzed to determine the amount of the target constituents present. The secondary device may comprise a suitable analytical technique or instrument or combination of analytical techniques or instruments. Such secondary devices may include gas chromatographs, high pressure liquid chromatographs, ion chromatographs, an optical emission or atomic absorption spectrograph or mass spectrometer, or radioanalytical instrumentation such as an alpha spectrometer, liquid scintillation spectrometer, gamma spectrometer or gas proportional counter, or any other instrument and technique appropriate to detect the targeted constituent. Additionally, a second stationary phase, or other solid-phase extraction system may be used to further remove or discriminate against unwanted constituents from the solution or more thoroughly isolate the target constituents.

Where one of more target constituents are to be captured on the stationary phase, as opposed to allowing the target constituents to pass while removing interfering constituents, the target constituents may be further purified on the stationary phase by selectively stripping impurities bound on the stationary phase. This further purification may be accomplished by passing a rinsing agent or agents through the membrane to change the conditions such that the affinity of the impurity for the binding agent is weakened relative to that of the target constituents.

For example, a load solution that is known or suspected to contain the target constituents in a physical and chemical form that will facilitate its binding to the binding agent, may be passed across the ePTFE membrane. Interfering constituents may be removed by allowing them to pass through the system without reaction or eluted from the stationary phase by passing an appropriate stripping agent or agents across the membrane. Bound target constituents may be eluted from the stationary phase by passing a stripping agent or agents across the membrane. As such, the stripping agent or agents selectively reduce the respective affinity of the interfering and target constituents for the binding agent thereby causing it to partition to the carrier solvent and flow from the membrane. Rinsing and stripping agents may include any agent, or agents in combination or series, which facilitate solubility of the target constituents in the carrier solvent as the carrier solvent passes through the membrane. However, the agent, or agents in combination or series, should be selected to facilitate selective separation and purification of the target constituents.

Rinsing and stripping agents may include more or less concentrated solutions or higher volumes of the preparatory agents, solutions that alter the pH of the solution, or appropriate complexing or chelating agents. For example, where the preparatory agent is an acidifying agent such as 3 molar hydrochloric acid, the rinsing agent may comprise a 0.5 molar solution of hydrochloric acid, or a redox reagent such as a nitrite or iodide, or a complexing agent such as an oxalate, or a chelating reagent such as EDTA, or other such reagents as are needed to facilitate the separation being performed.

A stripping agent (whose selection is analogous to the chemical techniques previously described for rinsing) may also be passed through the stationary phase. The stripping agent is selected such that upon passing the stripping agent through the membrane, the target constituents are released from the binding agent and passes through the stationary phase membrane to the outer surface of the membrane in the eluate. The eluate solution accumulates and may be recirculated through the same systems, collected for processing by a secondary device for further separation, concentration, purification, or for quantification or analysis of the target constituents, as present. The secondary device may comprise a suitable analytical technique or instrument or combination of analytical techniques or instruments. Such secondary devices may include gas chromatographs, high pressure liquid chromatographs, ion chromatographs, an optical emission or atomic absorption spectrograph or mass spectrometer, or radioanalytical instrumentation such as an alpha spectrometer, liquid scintillation spectrometer, gamma spectrometer or gas proportional counter, or any other instrument and technique appropriate to detect the targeted constituent. Additionally, a second stationary phase, or other solid-phase extraction system may be used to further remove or discriminate against unwanted constituents from the solution or more thoroughly isolate the target constituents. Finally, the system can be regenerated for reuse.

In each case, the load, rinse, and stripping solutions are caused to move across the ePTFE membrane by creating a pressure gradient across the membrane. Several examples of devices that could be used to include a syringe, a peristaltic pump, a downstream vacuum source, or even gravity flow.

The solid-phase extraction system may also include a kit for use in the field. The kit may include a stationary phase, a syringe, a plurality of adapters for attaching the syringe to the stationary phase, a system of preparatory agents, a plurality of collection vials, a system of stripping agents and packaging materials. Additionally, the kit may include portable analytical instrumentation or material and supplies for other field analytical techniques.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
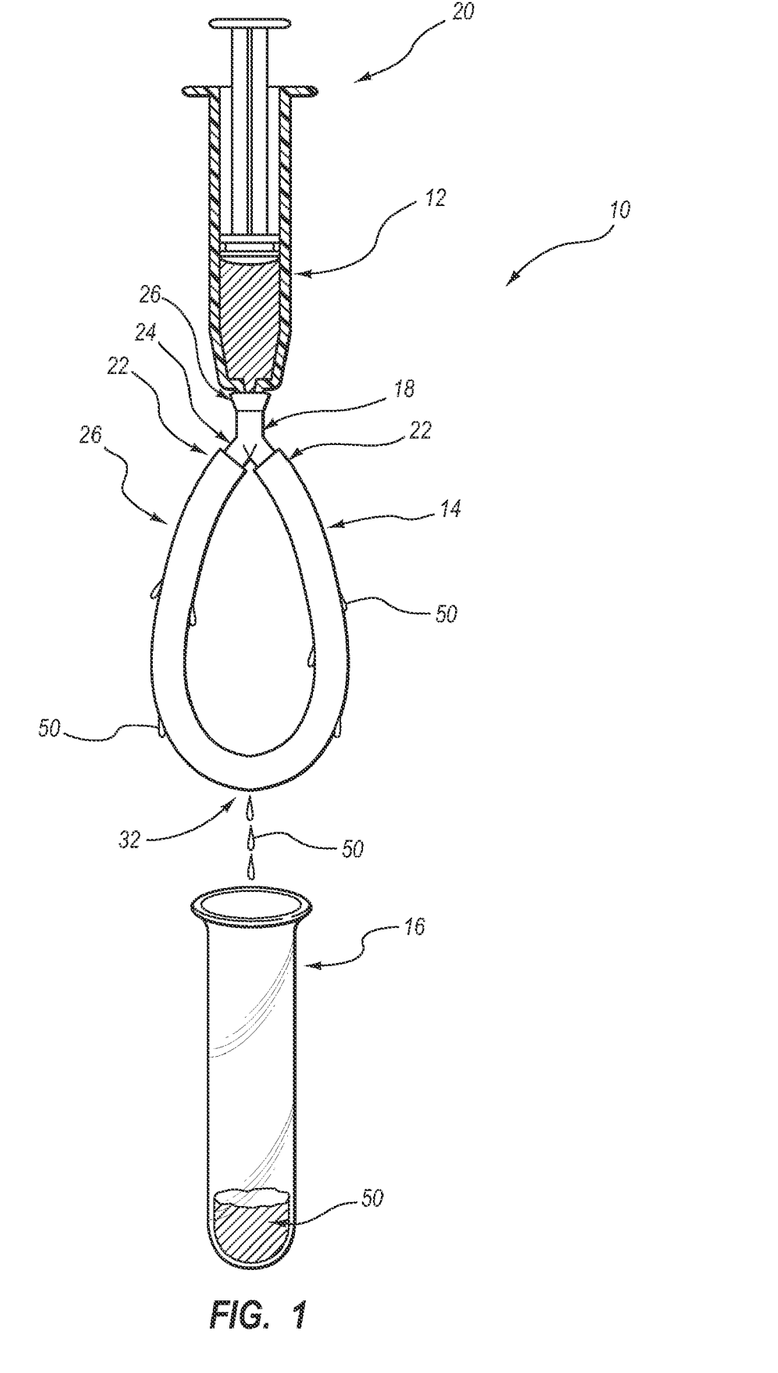
FIG. 1 is a perspective view of a solid-phase extraction system incorporating a section of ePTFE tubing in a loop configuration.
Figure 2:
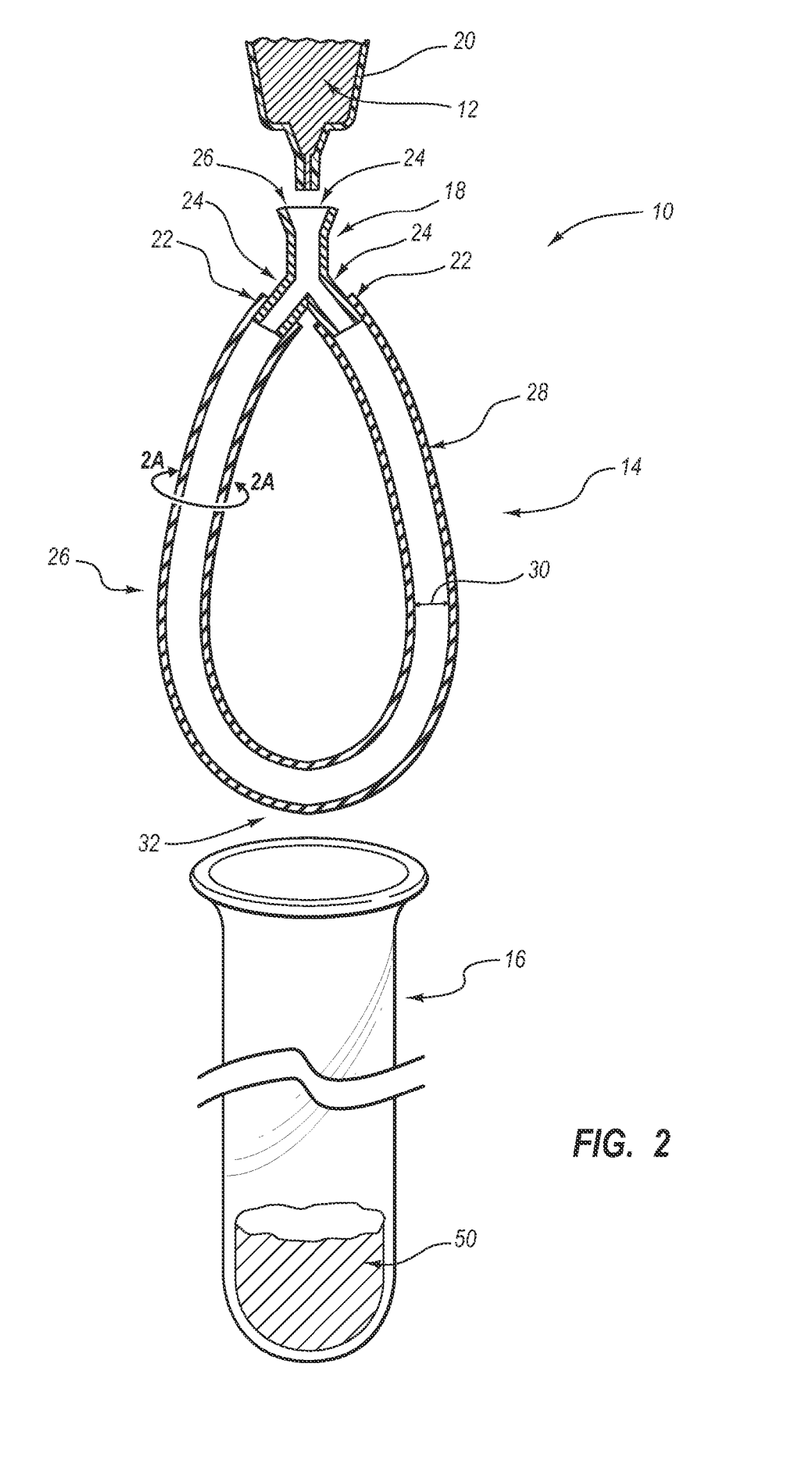
FIG. 2 is a cross-section view of the ePTFE tubing in a loop configuration as coupled to a y-adapter.

Referring now to FIGS. 1 and 2, a solid-phase extraction system 10 is illustrated. The solid-phase extraction system 10 comprises a mobile phase 12, a stationary phase 14, and a collection vial 16. The system 10 may also include a plurality of adapters 18 for establishing fluid communication between the various components of the system 10. Additionally, the system 10 may be exposed, as illustrated, or enclosed within a casing or another piece of equipment. For example, the system 10 may be incorporated into or used in tandem with a secondary device such as a suitable analytical technique or instrument or combination of analytical techniques or instruments. The secondary device may comprise a suitable analytical technique or instrument or combination of analytical techniques or instruments. Such secondary devices may include gas chromatographs, high pressure liquid chromatographs, ion chromatographs, an optical emission or atomic absorption spectrograph or mass spectrometer, or radioanalytical instrumentation such as an alpha spectrometer, liquid scintillation spectrometer, gamma spectrometer or gas proportional counter, or any other instrument and technique appropriate to detect the targeted constituent 54. Additionally, a second stationary phase, or other solid-phase extraction system may be used to further remove or discriminate against unwanted constituents from the solution or more thoroughly isolate the target constituents. The system 10 may also include a pump source, such as a peristaltic pump or a vacuum source as discussed in detail below.

The matrix 12 may consist of any number of materials including urine, blood, water samples, beverages, soil, animal tissues, consumer products, and modified or unmodified aqueous solution or leachates or digestates of other solid or liquid matrices that contain the target constituents. The matrix 12 may also contain a wide variety of analytes or constituents of interest. Constituents of interest present in the matrix 12 may include any number of isotopes or radioisotopes. Conceptually, the constituents 54 of interest may include any element on the periodic table, or isotope on the chart of the nuclides, in any chemical form (e.g., element, ion, complex, chelate, or compound) that is chemically or physically active with regard to the selected binding agent 52. For example, the matrix 12 may contain any actinide, lanthanide, transition metal, halide, alkaline earth or alkaline metal, noble gas, or any other element, or ions, complexes or chelates thereof, with an affinity for the selected binding agent. Isotopic constituents are also commonly encountered in the matrix 12 in the area of analytical chemistry, including various isotopes or radioisotopes of carbon, zinc, mercury, copper, cadmium, chlorine, beryllium, mercury, strontium, manganese, cobalt, nickel, copper, zinc, gadolinium, germanium, arsenic, selenium, bromine, palladium, tin, antimony, tungsten, thallium, gold, platinum, astatine, iodine, lead, iron, francium, radium, barium, yttrium, lanthanum, cerium, neodymium, promethium, samarium, europium, thorium, uranium, americium, plutonium, curium, polonium, bismuth, magnesium, calcium, rubidium, cesium, thallium, actinium, iodine, chlorine, phosphorus, and mixtures thereof. Additionally, the matrix 12 may include any combination or modification of the above described constituent 54 elements. For example, the constituent 54 may be incorporated in natural or synthetic compounds comprising additional undisclosed elements. Finally, the matrix 12 may include organic compounds and biological compounds as well as other molecular compounds useful in immunoassay and radioimmunoassay techniques.

The matrix 12 may include any combination or modification of the above described elements. For example, the matrix 12 may comprise a material including one or more of the above described elements or a material including one or more the above described elements and an additional element. The constituent compounds within the matrix 12 may be naturally-occurring or synthetic, within the scope of the current invention.

The matrix 12 may be introduced to the solid-phase extraction system 10 by any number of methods, including using a syringe, a peristaltic pump, a downstream vacuum source, or even gravity flow. For example, as illustrated, the load solution 12 may be introduced to the system 10 by a syringe 20. The syringe 20 may include a common medical syringe comprising a barrel made of plastic or glass, as known in the art. The load solution 12 is preloaded into the syringe 20 and the syringe 20 is attached to the stationary phase 14 via an adapter 18. The load solution 12 is transferred to the stationary phase 14 as the syringe 20 is actuated thereby creating a positive pressure and forcing the matrix 12 through the microscopic pores of the stationary phase 14.

Alternatively, the load solution 12 may be introduced to the system 10 via a remote sample reservoir and a length of tubing providing fluid communication between the sample reservoir and the system 10. As so configured, a pump or vacuum system may be needed to force or draw the load solution 12 through the stationary phase 14. For example, a downstream source of vacuum may be applied to the outer surface of the stationary phase 14 to pull the fluid matrix 12 through the microscopic pores from the upstream side, or inner surface of the stationary phase 14. Additionally, the load solution 12 may be loaded onto the solid phase 14 by gravity feed or another method as known in the art. If the constituents are present in the matrix in a form amenable to extraction, the matrix itself may be processed directly though system 10 as described above, or may be prefiltered prior to processing.

The stationary phase 14 of the current invention comprises a section of expanded polytetrafluoroethylene (ePTFE) tubing as illustrated. Although illustrated in a looped configuration, one of ordinary skill in the art will appreciate that the stationary phase 14 of the current invention may also be utilized in a linear configuration. The section of ePTFE tubing 26 is coupled to the remainder of the system 10 via an adapter 18. The adapter 18 is generally tubular with an outer diameter configured to compatibly insert into a first end 22 of the ePTFE tubing. Additionally, the adapter 18 comprises an access port 24 for compatibly receiving a syringe 20 or another means of introducing the load solution 12 to the system 10.

The adapter 18 may comprise any suitable polymer compatible with the load solution 12. Additionally, the polymer material of the adapter 18 must withstand the internal pressures of the system 10 created by the use of a pump or a vacuum. For example, the adapter 18 material may include a porous or non-porous, rigid or semi-rigid, polymer such as polystyrene, polypropylene, polyethylene, polytetrafluoroethylene, fluorinated ethylene-propylene, perfluoroalkoxy polymer, polyvinylchloride, polyvinylidene fluoride, nylon, and polycarbonate. The adapter 18 may be structured to adapt to any configuration needed within the system 10. For example, the adapter 18 may be y-shaped to accommodate a looped configuration of the ePTFE tubing 26, as illustrated.

Figure 2A:
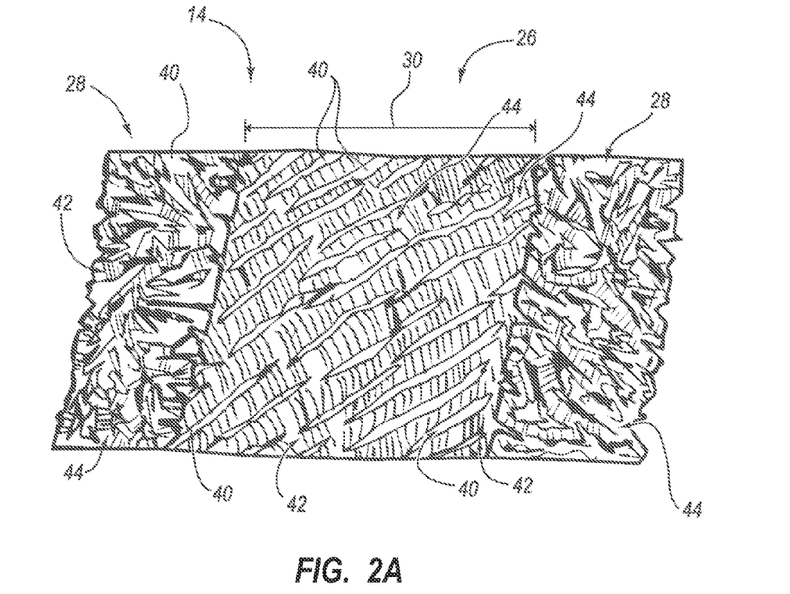
FIG. 2a is a detailed cross sectional view of FIG. 2 illustrating the structural characteristics of the ePTFE tubing.

As shown in FIGS. 2 and 2a, the ePTFE tubing 26 further comprises a tube wall 28, an inner diameter 30, and a tube length. The tube wall 28 comprises a uniform thickness of about 0.4 to 0.5 mm, although a thicker or thinner tube wall 28 may be used. The inner diameter 30 of the ePTFE tubing may range from about 0.01 mm to about 100 mm with a preferred inner diameter of about 1 mm. The tube length, as well as other dimensional features of the ePTFE tubing may vary greatly dependent upon the specific application. The system 10 may also be configured to include a first ePTFE tubing comprising an inner diameter greater than an outer diameter of a second ePTFE tubing. As such, the second ePTFE tubing may be inserted into the inner lumen of the first ePTFE tubing for simultaneous two-stage extraction procedures.

Figure 2B:
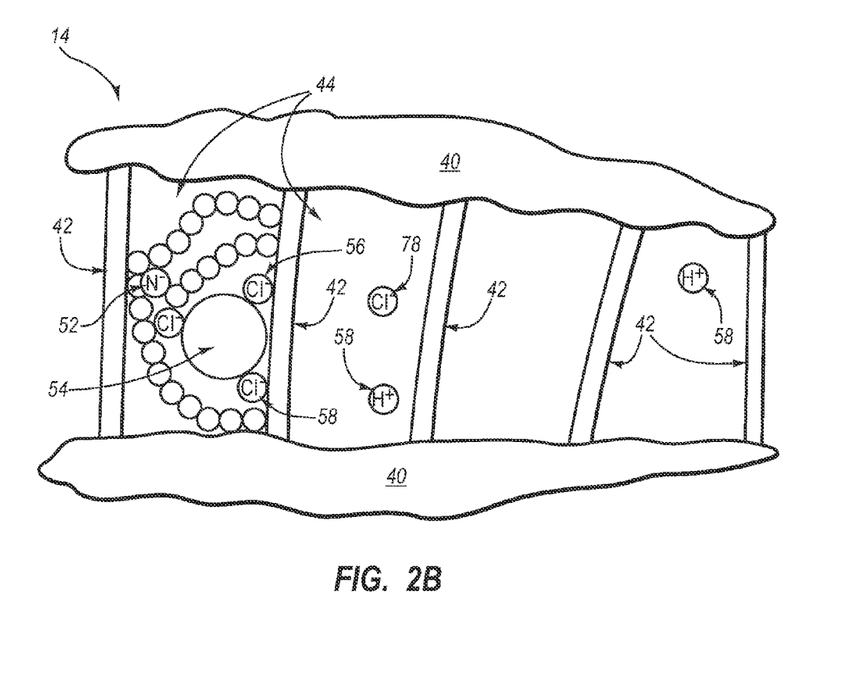
FIG. 2b is a detailed cross sectional view of FIG. 2a illustrating a molecule or binding agent impregnated within the microscopic pores of the ePTFE tubing.

Referring now to FIGS. 2a and 2b, the ePTFE tubing 26 is formed by heating and rapidly expanding a polytetrafluoroethylene tubing precursor material to form a microstructure of microscopic pores 40 interconnected by polymeric fibrils 42 with microscopic pores 44 therebetween. The microscopic pores 40 may vary in size from about 400 microns to less than a micron, depending upon the conditions used in the expansion. Likewise, the polymeric fibrils may comprise a maximum width of about 0.1 micron (1000 angstroms) and a minimum width of about one to two molecular diameters (~5 to 10 angstroms). Thus, the microstructure results in a stationary phase through which an eluate 50 may flow and be collected.

Referring now to FIG. 2b, the microstructure of the ePTFE tubing 26 may be modified to include a binding agent 52. The specific molecular characteristics of the binding agent 52 is selected based upon the binding agent's 52 ability to attract, sequester, associate, coordinate, or bind a desired constituent 54. Thus, the size, hydrophobicity, and molecular properties of the binding agent 52 is selected based on the desired constituents 54. Ultimately, the binding agent 52 may comprise any molecule or element of sufficient hydrophobicity to form an association with the ePTFE material and to minimize partitioning into an aqueous phase. For example, in one embodiment binding agents 52 include hydrophobic liquid organic extractants consisting of aliphatic quaternary amines (e.g., tricaprylyl-methylammonium chloride [Aliquat-336®], triisotylamine [TIOA], tri-noctylamine, [TnOA]), organophosphate complexing agents (such as octyl(phenyl)-N,N-diiso-butylcarbamoyl-methyl-phosphine oxide [CMPO]; tributylphosphate (TBP), trioctylphosphinic oxide (TOPO)), chelating agents, crown ethers, or antibodies, or other binding agents found suitable for the purposes of the separation to be conducted. The size and hydrophobicity of the binding agent 52 will determine the efficiency of the system in separating a constituent 54 from the load solution 12. For example, the molecular structure of the binding agent 52 must be compatible so as to impregnate within the microscopic pores 44 of the ePTFE tubing 26, as illustrated. Additionally, the degree of hydrophobicity of the binding agent 52 will determine the stability of the extractant on the surface of the ePTFE tubing 26.

Once selected, the binding agent 52 is impregnated within the microscopic pores 44 of the ePTFE tubing 26 by exposing the ePTFE tubing 26 to the binding agent 52 that is dissolved in a suitable solvent or mixture of solvents. For example, in one embodiment generally hydrophobic liquids such as acetone, hexane, octanol, or a combination thereof are used. The solution containing the binding agent 52 may be forced through the microscopic pores 44 of ePTFE tubing 26 via positive pressure using a syringe, a pump, gravity feed or other means that effect flow of fluid across the walls of the tubing. Additionally, the solution containing the binding agent 52 may be drawn through the microscopic pores 44 of the ePTFE tubing 26 via negative pressure, for example by placing a vacuum on the outer surface of the tubing. The process of forcing and/or drawing the binding agent 52 through the ePTFE tubing 26 allows the hydrophobic binding agent 52 to come into contact with the hydrophobic ePTFE tubing and to bond via hydrophobic exclusion. Once bound, the binding agent 52 and the ePTFE tubing 26 together constitute the stationary phase 14 of the solid-phase extraction system 10.

Constituents of interest present in the matrix may include any isotope and radioisotopes. Conceptually, the constituent 54 of interest may include any element on the periodic table, or isotope on the chart of the nuclides, in any chemical form (e.g., element, ion, complex, chelate, or compound) that is chemically or physically active with regard to the selected binding agent 52. For example, the matrix 12 may contain any actinide, lanthanide, transition metal, halide, alkaline earth or alkaline metal, noble gas, or any other element, or ions, complexes or chelates thereof, with an affinity for the selected binding agent. Isotopic constituents are also commonly encountered in the area of analytical chemistry including various isotopes or radioisotopes of carbon, zinc, mercury, copper, cadmium, chlorine, beryllium, mercury, strontium, manganese, cobalt, nickel, copper, zinc, gadolinium, germanium, arsenic, selenium, bromine, palladium, tin, antimony, tungsten, thallium, gold, platinum, astatine, iodine, lead, iron, francium, radium, barium, yttrium, lanthanum, cerium, neodymium, promethium, samarium, europium, thorium, uranium, americium, plutonium, curium, polonium, bismuth, magnesium, calcium, rubidium, cesium, thallium, actinium, iodine, chlorine, phosphorus, and mixtures thereof. Additionally, the matrix may include any combination or modification of the above described constituent 54 elements. For example, the constituent 54 may be incorporated in natural or synthetic compounds comprising additional undisclosed elements. Finally, the matrix may include organic compounds and biological compounds as well as other molecular compounds useful in immunoassay and radioimmunoassay techniques.

The constituent 54 elements within the matrix may require modifications in order to properly bind the binding agent 52. Therefore, the matrix 12 containing the constituent 54 elements may require treatment to ensure that the target constituent 54 is transformed to, or maintained in, a physical and chemical state that facilitates its association with the binding agent 52 and which may minimize or eliminate the effects of interfering or competing constituents and reactions. For example, in one embodiment the matrix 12 requires treatment with one or more preparatory agents appropriate to the binding agent 52 and chemical separation desired. Common preparatory agents may include acids, bases, oxidizing or reducing agents, as well as complexing or chelating agents, such as EDTA or DTPA or other such reagents as are needed to facilitate the separation being performed. For example, in one embodiment where the solid-phase extraction is based on an anion exchange separation, the matrix 12 is treated with an appropriate reagent, such as hydrochloric acid, to form anions. Conversely, where the solid-phase extraction is based on a chelation theory, the matrix 12 is treated with appropriate preparatory agents to ensure that the constituents are in a form amenable to chelation. Once all preparation is complete, the resulting solution is called the 'load solution' which can be loaded onto the stationary phase 14, as described above.

Figure 3:
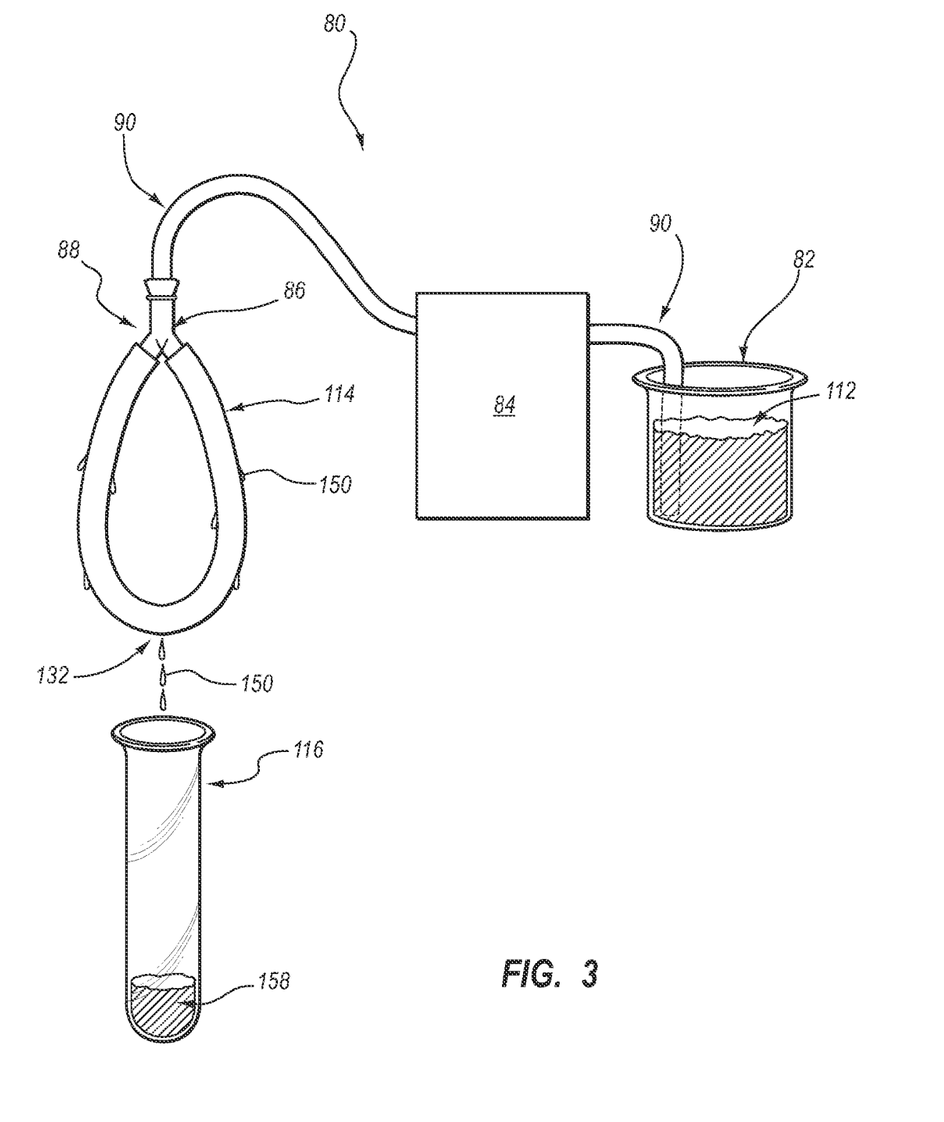
FIG. 3 is a perspective view of the ePTFE tubing as incorporated into a system including a pump source.

Referring now to FIGS. 2b and 3, the load solution 12 may be loaded onto the stationary phase 14 as a load solution. A load solution may consist of modified or unmodified aqueous solutions, leachates, or digestates of other matrices, such as solids or liquids, which contain the constituents 54 of interest. The load solution may be loaded onto the stationary phase 14 via a syringe, a pump or a vacuum source, as previously discussed. As the load solution 12 is forced through the microscopic pores 44 of the ePTFE tubing, the solution containing any unbound constituents in the load solution pass through the membrane and collect on the external surface of the membrane until droplets 150 (see FIG. 3) form that may be recirculated through the same system or collected in a vial 116. The collected solution 158 may be further processed by a secondary device or analyzed to determine the amount of the target constituents 54 present. The secondary device may comprise a suitable analytical technique or instrument or combination of analytical techniques or instruments. Such secondary devices may include gas chromatographs, high pressure liquid chromatographs, ion chromatographs, an optical emission or atomic absorption spectrograph or mass spectrometer, or radioanalytical instrumentation such as an alpha spectrometer, liquid scintillation spectrometer, gamma spectrometer or gas proportional counter, or any other instrument and technique appropriate to detect the targeted constituent. Additionally, a second stationary phase, or other solid-phase extraction system may be used to further remove or discriminate against unwanted constituents from the solution or more thoroughly isolate the target constituents.

Referring again to FIG. 2b, a target constituent 54 may be captured on the stationary phase 14, as opposed to allowing the target constituent 54 to pass while removing interfering constituents. The target constituent 54 may be further purified on the stationary phase 14 by selectively stripping impurities bound on the stationary phase 14. This further purification may be accomplished by passing a rinsing agent or agents through the membrane to change the conditions such that the affinity of the impurity for the binding agent 52 is weakened relative to that of the target constituent 54.

For example, in one embodiment a load solution that is known or suspected to contain the target constituent 54 in a physical and chemical form that will facilitate it's binding to the binding agent 52, is passed across the ePTFE membrane. Interfering constituents may be removed by allowing them to pass through the system without reaction or eluted from the stationary phase by passing an appropriate stripping agent or agents across the membrane. Bound target constituent 54 is then eluted from the stationary phase 14 by passing a stripping agent or agents across the membrane. As such, the stripping agent or agents reduce the affinity of the target constituent 54 for the binding agent 52 thereby causing the target constituent 54 to partition the carrier solvent and flow from the membrane.

Rinsing and stripping agents may include more or less concentrated solutions or higher volumes of the preparatory agents, solutions that alter the pH of the solution, or appropriate complexing or chelating agents. For example, where the preparatory agent is 3 molar hydrochloric acid, the rinsing agent may comprise a 0.5 molar solution of hydrochloric acid or a redox reagent such as nitrate or iodine, or a complexing agent such as an oxalate, or a chelating reagent such as EDTA, or other such reagents as are needed to facilitate the separation being performed.

Referring now to FIG. 3, another embodiment of a solid-phase extraction system 80 is illustrated. The system 80 includes a stationary phase 114, a sample vial 82, an inline device 84, a plurality of adapters 86 and a collection vial 116. The stationary phase 114 comprises a section of ePTFE tubing identical to that described in connection with the solid-phase extraction system 10, above. The sample vial 82 stores the load solution 112 and may comprise glassware or a plastic container compatible with the load solution 112. The sample vial 82 may be open, as illustrated, or enclosed to protect the load solution 112. The plurality of adapters 86 establishes fluid communication between the stationary phase 114 and the remainder of the system 80. Unlike the previous plurality of adapters 118, the illustrated plurality of adapters 86 comprises a third end 88 configured to couple a length of tubing 90. Additionally, the third end 88 may be configured to universally couple to a variety of adapters commonly used to interconnect tubing, syringes and the like as used in the art of glassware and vacuum tubing.

The inline device 84 may comprise a variety of functions. For example, the inline device 84 may include a pump, such as a peristaltic pump, as well as a secondary device, as described in detail above. The inline device 84 may also provide an internal cavity for housing the stationary phase 114 and the collection vial 116 during use of the system 80. As illustrated, the sample vial 82 and the stationary phase 114 are in fluid communication via a first and second length of tubing 90. The length of tubing 90 may include a flexible, semi-rigid or rigid, high-pressure vacuum tubing compatible with the load solution 112 and the function of the inline device 84.

Additional features of the system 80 may include a post-stationary phase analysis including additional equipment or devices for analyzing or further purification of the constituent 54 containing solution 150. For example, additional equipment or devices may include devices such as gas chromatographs, high pressure liquid chromatographs, ion chromatographs, an optical emission or atomic absorption spectrograph or mass spectrometer, or radioanalytical instrumentation such as an alpha spectrometer, liquid scintillation spectrometer, gamma spectrometer or gas proportional counter, or any other instrument and technique appropriate to detect the targeted constituent.

Figure 4:
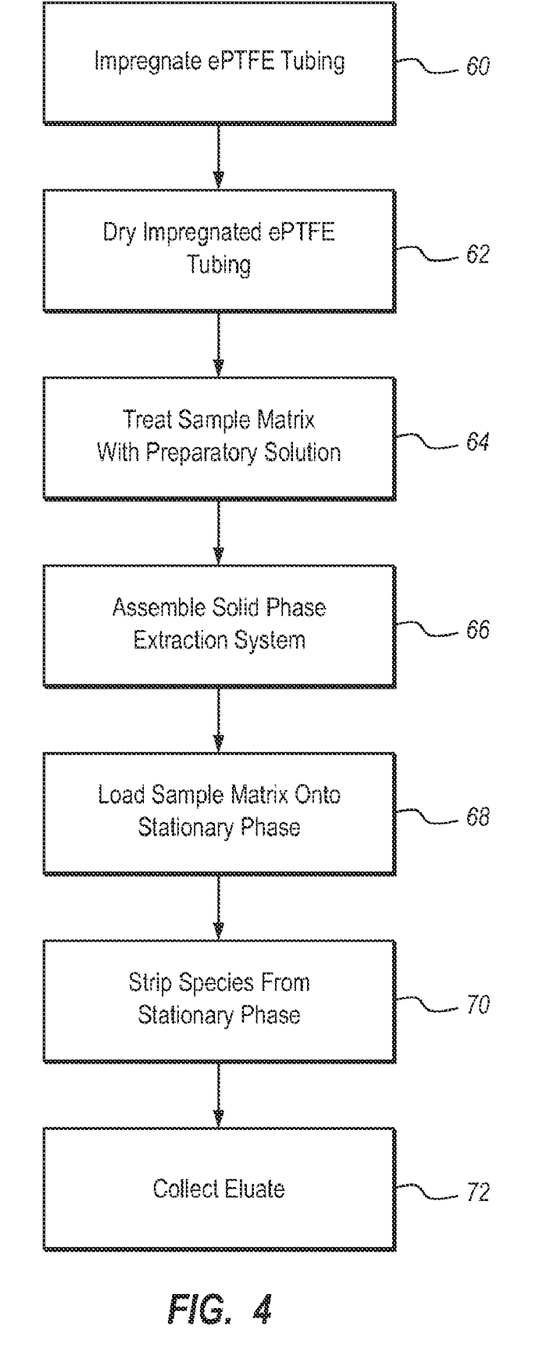
FIG. 4 is a flow chart detailing one implementation for preparing and using the ePTFE tubing.

Referring now to FIG. 4, a flow chart is provided detailing the process for preparing and using the solid-phase extraction system. The first step 60 of the process involves impregnating a section of ePTFE tubing with a selected binding agent. The ePTFE tubing may be impregnated by forcing a solution of the binding agent through the ePTFE tubing via a syringe, a pump or a vacuum, or even by simply soaking the tubing in the solution of binding agent. The solution containing the binding agent may be comprised of the binding agent itself, or a solvent or mixture of solvents in which the binding agent may be dissolved. For example, in one embodiment hydrophobic solvents, such as acetone, hexane, octanol, or combinations of hydrophobic liquids, is used. In another embodiment, a binding agent solution comprising 50% acetone and 50% binding agent is provided. Additional concentrations of binding agent may also be used effectively within the scope of this invention. In another embodiment, the ePTFE tubing is soaked in the binding agent solution for an extended period of time to effectuate impregnation.

Following impregnation, the second step 62 involves drying the impregnated ePTFE tubing. Drying the ePTFE tubing may be desirable for several reasons. For instance, drying the ePTFE tubing allows the volatile solvent to evaporate thereafter leaving only the binding agent impregnated within the microscopic pores. In the absence of the hydrophobic environment of the solvent, the binding agent associates more tightly with the hydrophobic ePTFE material. Drying the ePTFE tubing may also permit a measurement of the amount of binding agent impregnated within the ePTFE tubing.

A third step 64 involves treating a matrix containing the target constituents. This step is accomplished by treating the matrix with an agent or solution to ensure that the target constituent is transformed to, or maintained in a physical and chemical state that facilitates its association with the binding agent and other solid-phase extraction system that may be used to further remove any unwanted constituents from the solution or more thoroughly isolate the target constituents. For example, in one embodiment a matrix is treated with hydrochloric acid to a final concentration of approximately 3 molar hydrochloric acid to cause the formation of anions in solution. Once all preparation steps are complete, the solution containing the constituents of interest is termed the load solution. Following the treatment step, the load solution is loaded into a syringe or other device, for introduction to the solid-phase extraction system.

A fourth step 66 involves assembling the solid-phase extraction system. Generally, this step involves establishing a fluid communication between the various components and sub-components of the system. For example, as illustrated in FIG. 1, a user will attach the ePTFE tubing 26 to a first and second end 24 of an adapter 18. The user will then couple a syringe 20 or another device to a third end 26 of the adapter 18. The specifics of this step will depend largely on the selected configuration of the system. For example, where a system includes a pump, a vacuum source, an enclosure or a secondary analytical device, the step 66 of assembly will have to be adjusted accordingly.

The fifth step 68 is to introduce the load solution into the ePTFE tubing. Having been impregnated with the binding agent, the ePTFE tubing comprises the stationary phase of the system. Certain constituents will associate, coordinate or bind to the stationary phase of the system while other constituents will pass through in the eluate. Depending upon the specific application of the system, the eluate may be the desired product or may be a waste product. Where the application of the system is to purify a liquid of a target constituent by removing unwanted constituents, the eluate following this step 68 is the desired, purified product. Where the application of the system is to chemically separate target constituents from a solution, the eluate following this step 68 is a waste product and may be discarded or preserved for other processing.

In applications of the system where the goal is to chemically separate target constituents by extracting onto the stationary phase, the sixth step 70 is to further purify target constituents contained on the stationary phase by rinsing the stationary phase by passing a rinsing agent through the membrane to remove unwanted constituents that exhibit affinity for the binding agent under the conditions present in the load solution. The unwanted constituents are rinsed from the stationary phase is by forcing the rinsing solution through the stationary phase and thus creating conditions that will selectively remove unwanted constituents while retaining wanted constituents on the stationary phase. For example, in one embodiment rinsing agents comprise more or less concentrated solutions of the preparatory agent or agents, or complexing, chelating or oxidation/reduction reagents. In another embodiment, where the preparatory agent is an acidifying agent such as 3 molar hydrochloric acid, the rinsing agent comprises a 0.5 molar solution of hydrochloric acid, or a solution of nitric acid, or a redox agent such as a nitrite or iodine, or a complexing agent such as an oxalate, or a chelating reagent such as EDTA, as are found in the art of chemical and radiochemical separations. The rinsing solution weakens the affinity of the impurity for the binding agent relative to the affinity of the target constituents. As such, the unwanted impurities are released from the stationary phase without releasing the target constituents. Any number of rinses, as well as various rinsing agents, may be used as determined by the user to be optimal for the chemical separation being performed.

In the seventh step, target constituents may be selectively released, or stripped from the stationary phase by forcing a stripping solution through the system. The stripping agent may be passed through the membrane of the system by a method as discussed in connection with the load solutions above (e.g., syringe, pump, vacuum, or gravity feed). A rinsing solution creates conditions that remove target constituents while retaining unwanted constituents on the stationary phase. The stripping agents (whose selection is analogous to the chemical techniques to those previously described for rinsing) may also be passed through the stationary phase.

The last step 72 involves collecting the target constituents-containing eluate in a collection vial. Again, depending upon the specific application of the system, the eluate may be collected in a vial or a secondary analytical device as required by the system. The eluate may be collected concomitantly with the previous step 70. For example, in one embodiment the stripping solution reduces the affinity of the target constituents for the binding agent thereby releasing the target constituent from the stationary phase. Once released, the target constituent collects on the outer or downstream surface of the membrane where the target constituent is collected with the eluate.

EXAMPLES

Additional objects, advantages, and novel features of this invention will become apparent to those skilled in the art upon examination of the following examples thereof. It should be appreciated that these examples are not to be considered as limiting the scope of the invention, but merely as being illustrative and representative thereof.

Example 1

Solid-Phase Extraction System with N-methyl-N,N,N'trioctylammonium chloride Binding Agent Step 1: Impregnation of ePTFE Tubing Two ends of a 25 cm length of ePTFE tubing (2 mm O.D. and 1 mm I.D.) were coupled to a first and second arm of a Y connector thereby forming the ePTFE tubing into a looped configuration.

A 50% binding agent solution of N-'methyl-N,N, N'trioctylammonium chloride in acetone was prepared. The binding agent solution was transferred to a 5 ml syringe and the syringe was coupled to the third arm of the Y connector. The binding agent solution was forced through the microscopic pores of the ePTFE tubing using the 5 ml syringe. The ePTFE tubing loop was detached from the 5 ml syringe and the loop was stored immersed in the binding agent solution until it was to be used for sample processing In order to process a sample solution the loop was removed from the binding agent solution and excess binding agent solution was removed in two steps. The first step was to reconnect the third arm of the Y connector to a 5 ml syringe filled with air and force air through the microscopic pores of the tubing. The second step was to disconnect the 5 ml syringe and connect the third arm of the Y connector to a peristaltic pump. Approximately 100 ml of 0.1N HCl was pumped through the microscopic pores to further remove excess binding agent. Droplets which formed on the outside of the tubing when the 0.1N HCl solution was pumped through the tubing were collected in a funnel to facilitate collection.

Step 2: Preparing Analyte Test Solution

An analyte test solution was prepared to simulate a solution matrix resulting from the dissolution of a soil sample. The test solution contained the following constituents: 0.5 g $FeCl_3.6H_2O$; 2 g boric acid; 20 dpm Pu-242; 50 µg natural U; 50 µg natural Th; 10 ml concentrated nitric acid; 140 ml water. 20 ml of concentrated ammonium hydroxide was added to form an $Fe(OH)_3$ precipitate which co-precipitated the Pu, U, and Th. The precipitate was dissolved with 3 ml of concentrated nitric acid and then the solution was diluted to 15 ml with water. This produced a solution (the load solution) with a nitric acid concentration of approximately 3.2M.

Step 3: Loading Pu and Th onto the Stationary Phase

The 3.2M $HNO_3$ load solution was pumped through the tubing at 7 ml/minute (this flow rate was used throughout this example). 3 ml of 3.5M $HNO_3$ was then pumped through the tubing to rinse un-reacted constituents from the tubing. Pu and Th were retained by the tubing and U passed through the tubing. The pumping time required to load Pu and Th was about 3 minutes.

Step 4: Releasing Th from the Stationary Phase

Th was released from the tubing by pumping 10 ml of 3 molar HCl through the tubing in two separate 5 ml fractions. Each fraction was collected separately and was analyzed by ICP-AES. The results are summarized below.

| Thorium Recovery | |
|---|---|
| Fraction | % Recovery |
| 1 | 91 |
| 2 | 7 |
| Overall Recovery: | 98% |

Pumping time required to release Th was about 2 minutes.

Step 5: Releasing Pu from the Stationary Phase

Pu was released from the tubing by pumping 10 ml of 0.01M ammonium oxalate through the tubing. A lanthanum fluoride micro-precipitation was performed directly in the stripped 0.01M ammonium oxalate solution to prepare a source for alpha spectrometry. The Pu recovery determined by alpha spectrometry was 91%. Pumping time to release Pu was about 2 minutes.

Step 6: Loading U onto the Stationary Phase

The solution which passed through the tubing in Step 3 was collected in a beaker. The solution was evaporated to dryness to remove nitric acid. The residue was then dissolved in 1 ml of concentrated HCl followed by 9 ml of water. 0.5 g of ascorbic acid was added to reduce $Fe^{3+}$ to $Fe^{2+}$ and then 4.4 g of $CaCl_2.2H_2O$ was added to produce an approximate chloride concentration of 3 molar. This solution was pumped through the tubing to load U onto the stationary phase. Pumping time required to load U was about 2 minutes.

Step 7: Releasing U from the Stationary Phase

U was released from the tubing by pumping 10 ml of 3.5M $HNO_3$ through the tubing in two separate 5 ml fractions. Each fraction was collected separately and was analyzed by ICP-AES. The results are summarized below.

| Uranium Recovery | |
|---|---|
| Fraction | % Recovery |
| 1 | 73 |
| 2 | 16 |
| Overall Recovery: | 89% |

Pumping time required to release U was about 2 minutes.

Step 8: Preparing the ePTFE Tubing for Processing Another Sample

The tubing can be prepared for processing another sample solution by pumping about 20 ml of a 1% $HNO_3$, 1% HCl solution through the tubing to thoroughly rinse the tubing. The tubing is now ready for processing another sample. The binding agent is strongly retained on the ePTFE. More than 1500 ml of various solutions have been pumped through the impregnated tubing used in this example.

Step 9: Storing the Impregnated ePTFE Tubing

Rinse the tubing by pumping about 20 ml of a 1% $HNO_3$, 1% HCl solution through the tubing and then pump air through the tubing.

Example 2

Two-Stage Extractions

Using the same extraction principles described in Example 1, two ePTFE stationary phases containing two complementary extracts could be used in series without modifying the matrix, or with modifying the matrix using a manual or automated mixing devices (similar to those used in ICs, GCs or ICPs). By combining two extractants in sequence, increased specificity can be obtained. Additionally, higher decontamination from interferences can be achieved by adding a second stage, and using the same extractant in sequence.

Example 3

Flow System Extraction and Concentration for Flow Injection Systems

Measurements of radionuclides by Inductively Coupled Plasma Atomic Emission Spectrographs (ICP-AES), Inductively Coupled Plasma Atomic Mass Spectrometers (ICP-MS), liquid or gas chromatographs, optimally run in tandem with secondary detectors such as mass spectrometers, (e.g., GC-MS or LC-MS-MS) often require pre-concentration and chemical separation of the analyte, and clean-up from interfering constituents in the sample. Used in a refluxing mode with an appropriate extractant, this technique can chemically isolate (i.e., separate) the target analyte from a large volume of sample solution and simultaneously providing for decontamination from interfering constituents in solution. The analyte can then be eluted from the ePTFE stationary phase in a very small volume amenable to introduction into the instrument for measurement. Thus, the technique of preconcentrating the sample can achieve more sensitive measurements. By increasing the concentration of the analyte relative to interfering constituents, interfering effects, such as isobaric interference in mass spec measurements, or coelution of interfering constituents on chromatographic techniques, can be eliminated.

Example 4

Flow System Extractions by Coupling with Radiation Detection Systems

Very sensitive online measurements of penetrating radiations, including low energy gamma rays, x-rays and beta particles could be performed in near real-time by incorporating an ePTFE stationary phase in a flow system. Traditionally, detection of heavy elements such as the actinides and transuranic elements in process or coolant streams as well as pure beta-emitting radionuclides has been very difficult since alpha particles and the low energy gamma rays and x-rays are attenuated within the liquid matrix preventing reliable detection and measurement. The geometry provided by tiny cross-section of the ePTFE tubing represents a unique opportunity for on-line detection of these elements since it is small enough to allow the radiations to be emitted and detected without significant attenuation.

Applications may include on-line measurements of process, effluent, or coolant stream components and could also be used to monitor entrained radionuclides in a gas or vapor stream that have been removed by scrubbing or condensation. An ePTFE stationary phase may also be contained within (or situated adjacent to) the active volume of a radiation detector. Many different kinds of radiation detectors may be used, including solid state detectors such as high purity germanium (HPGe), or scintillation detectors such as NaI(Tl) or beta scintillators, or into a liquid scintillation detector (whereby a minimal volume of cocktail could be used significantly decreasing background and increasing sensitivity), or a into a gas detector such as an ion chamber, gas flow proportional or Geiger-Muller detector. Radiations emitted would interact with and be detected by the selected radiation detector. In the most favorable case, the detector would be machined to facilitate introduction and removal of the ePTFE stationary phase, such that the stationary phase is effectively surrounded by the active volume of the detector which will optimize energy transfer from emitted radiations and the efficiency of the detector. The ePTFE stationary phase may be enclosed within an outer tube that would channel liquid away from the stationary phase after it has passed though the tube.

Example 5

Measurement of Extracted Radionuclides by Liquid Scintillation Direct Counting

An ePTFE stationary phase with extracted radionuclide could be immersed directly into liquid scintillation cocktail and counted directly in a liquid scintillation detector. The intimate contact with the cocktail would permit ultra sensitive detection of low-energy beta particles as well as alpha particles. Given the tiny cross-section of the ePTFE tubing, it would be possible to minimize the amount of cocktail to an absolute minimum and thus significantly drop the background and improve the signal-to-noise ratio and thus the sensitivity of the measurement relative to conventional LSC counting. Examples of analytes that could lend themselves to this may include low-energy beta emitters such as $^{99}Tc$, $^{147}Pm$ and $^{129}I$.

Finally, the present invention may include a kit for use in the field. The kit may comprise a stationary phase, a system of preparatory agents, a plurality of collection vials, a system of stripping agents and packaging materials. The kit may comprise one or more stationary phases. For example, the kit may include one stationary phase for use as an anion exchanger, and another stationary phase for chelation. Additionally, the kit may include one or more lengths of unimpregnated ePTFE tubing and one or more binding agents. Thus, a user may customize the stationary phase of the solid-phase extraction system by impregnating the ePTFE tubing with a binding agent of choice.

The kit may also include a system of preparatory agents. The system of preparatory agents may include an acidifying agent or any other agent useful to preparing a matrix prior to loading. The kit may also include a system of stripping agents. The system of stripping agents may include various stripping agents compatible with the included preparatory agents as well as the chemical properties of the bound analytes. The packaging materials of the kit may be disposable or reusable within the scope of the current invention.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for chemically separating a target constituent from a matrix, the method comprising:
   impregnating a microscopic pore of a section of expanded polytetrafluoroethylene (ePTFE) tubing with a binding agent, the section of ePTFE tubing comprising a single membrane having an outer surface in direct communication with an exterior environment, the section of ePTFE tubing further having a lumen for receiving at least one of a preparatory agent and a matrix;
   optimizing binding of the target constituent to the binding agent by treating the matrix with a preparatory agent;
   loading the matrix onto the microscopic pore of the section of ePTFE tubing;
   binding the target constituent with the binding agent; and
   providing a container having an opening for receiving a sample from the outer surface of the single membrane; and
   providing a y-adapter having a first end, a second end, and a third end, and a lumen interconnecting the first and second ends of the y-adapter, the first end of the y-adapter being coupled to a first end of the section of ePTFE tubing, the second end of the y-adapter being coupled to a second end of the section of ePTFE tubing, the section of ePTFE tubing forming a loop, and the third end of the y-adapter being configured to receive at least one of the matrix, the preparatory agent, and a stripping agent.

2. The method of claim 1, wherein the microscopic pore of the section of ePTFE tubing is configured to be saturated with the binding agent.

3. The method of claim 1, wherein the target constituent is a contaminant within the matrix.

4. The method of claim 2, wherein the binding agent comprises a liquid organic extractant that binds the target constituent of the matrix.

5. The method of claim 4, wherein the binding agent is selected from a group consisting of an aliphatic quaternary amine, a crown ether, a chelating compound, and an antibody.

6. The method of claim 1, wherein the microscopic pore of the section of ePTFE tubing is configured to permit passage of at least a portion of the matrix.

7. The method of claim 6, wherein the microscopic pore is further configured to permit binding of prepared target constituent bound by the binding agent.

8. The method of claim 7, wherein the microscopic pore is further configured to permit passage of a stripping agent configured to release the target constituent from the binding agent.

9. The method of claim 8, further comprising a step for passing the stripping agent through the microscopic pore of the section of the ePTFE tubing to release the bound target constituent from the binding agent.

10. The method of claim 9, wherein the target constituent is selected from a group consisting of an actinide, a lanthanide, a transition metal, zinc, cadmium, beryllium, mercury, strontium, lead, iron, francium, radium, barium, polonium, bismuth, magnesium, calcium, rubidium, cesium, thallium, actinium, iodine, chlorine, phosphorus, and combinations and isotopes thereof.

11. The method of claim 1, further comprising the step of concentrating the target constituent during flow injection into at an analytical device selected from the group consisting of a liquid chromatograph, a gas chromatograph, a gas chromatograph mass spectrometer, an inductively coupled plasma mass spectrometer, and an inductively coupled plasma atomic emission spectroscope.

12. The method of claim 11, wherein the step of concentrating the target constituent is achieved by at least one of a single-pass mode and a refluxing mode.

13. The method of claim 1, further comprising the step of analyzing the bound target constituent via an analytical device selected from the group consisting of a liquid scintillation spectrometer and a gamma spectrometer.

14. The method of claim 1, further comprising a step for integrating the section of ePTFE tubing into a radiation detection device selected from the group consisting of a gamma-ray spectrometer and an x-ray spectrometer.

15. The method of claim 14, wherein the section of ePTFE tubing is mechanically coupled to the radiation detection device.

16. The method of claim 1, wherein the section of ePTFE tubing further comprises a first end having an opening and further comprising a plurality of fibrils defining a plurality of microscopic pores, the microscopic pores collectively forming an outlet for the section of ePTFE tubing.

17. The method of claim 1, wherein the third end of the y-adapter is further configured to coupled to an apparatus for introducing at least one of the preparatory agent and the matrix to the lumen of the section of ePTFE tubing.

18. The method of claim 17, wherein the apparatus is a syringe.

* * * * *